(12) United States Patent
Horstmann et al.

(10) Patent No.: US 8,980,308 B2
(45) Date of Patent: Mar. 17, 2015

(54) TRANSDERMAL PHARMACEUTICAL PREPARATION CONTAINING ACTIVE SUBSTANCE COMBINATIONS, FOR TREATING PARKINSON'S DISEASE

(75) Inventors: Michael Horstmann, Neuwied (DE); Frank Theobald, Bad Breisig (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 1785 days.

(21) Appl. No.: 10/568,941

(22) PCT Filed: Aug. 14, 2004

(86) PCT No.: PCT/EP2004/009136
§ 371 (c)(1),
(2), (4) Date: Feb. 21, 2006

(87) PCT Pub. No.: WO2005/018619
PCT Pub. Date: Mar. 3, 2005

(65) Prior Publication Data
US 2007/0026054 A1   Feb. 1, 2007

(30) Foreign Application Priority Data
Aug. 20, 2003   (DE) .................. 103 38 174

(51) Int. Cl.
| A61K 9/70 | (2006.01) |
| A61K 31/13 | (2006.01) |
| A61K 31/381 | (2006.01) |
| A61K 31/428 | (2006.01) |
| A61K 45/06 | (2006.01) |

(52) U.S. Cl.
CPC .............. *A61K 9/7092* (2013.01); *A61K 31/13* (2013.01); *A61K 31/381* (2013.01); *A61K 31/428* (2013.01); *A61K 45/06* (2013.01)
USPC ........................................................ 424/449

(58) Field of Classification Search
None
See application file for complete search history.

(56) References Cited

U.S. PATENT DOCUMENTS

| 4,666,441 A | * | 5/1987 | Andriola et al. ............... 424/448 |
| 4,812,481 A | | 3/1989 | Reisching |
| 4,877,618 A | * | 10/1989 | Reed, Jr. ....................... 424/448 |
| 4,963,568 A | * | 10/1990 | Schoenleber et al. ........ 514/320 |
| 5,462,746 A | | 10/1995 | Wolter et al. |
| 5,614,178 A | * | 3/1997 | Bloom et al. .................. 424/60 |
| 5,807,570 A | * | 9/1998 | Chen et al. .................... 424/449 |
| 5,877,173 A | * | 3/1999 | Olney et al. ................... 514/217 |
| 5,902,601 A | | 5/1999 | Horstmann |
| 6,193,992 B1 | * | 2/2001 | El-Rashidy et al. .......... 424/430 |
| 2003/0082214 A1 | | 5/2003 | Williams |
| 2003/0119884 A1 | | 6/2003 | Epstein et al. |
| 2004/0013620 A1 | * | 1/2004 | Klose et al. ..................... 424/59 |
| 2007/0225379 A1 | * | 9/2007 | Carrara et al. ................ 514/756 |

FOREIGN PATENT DOCUMENTS

| CA | 2 383 509 | 3/2001 |
| DE | 3710966 | 12/1987 |
| EP | 0241809 B1 | 8/1990 |
| EP | B-0 404807 | 6/1993 |
| EP | 1 254 661 | 11/2002 |
| EP | A-1 256339 | 10/2003 |
| FR | 2788982 | 8/2000 |
| JP | S61145112 | 7/1986 |
| JP | S61186317 | 8/1986 |
| JP | A S62-249923 | 10/1987 |
| JP | A H02-503677 | 11/1990 |
| JP | A H11-506744 | 6/1999 |
| JP | H11506462 | 6/1999 |
| JP | A H11-209271 | 8/1999 |
| JP | A 2000-514053 | 10/2000 |
| JP | A 2001-39865 | 2/2001 |
| JP | 2001518058 | 10/2001 |
| JP | A 2002-97137 | 4/2002 |
| JP | 2003513014 | 4/2003 |
| JP | 2007502795 | 2/2007 |
| WO | WO 89/09051 | 10/1989 |
| WO | WO 9600062 A1 | 1/1996 |
| WO | WO 00/45795 | 8/2000 |
| WO | WO 00/74661 | 12/2000 |
| WO | WO 02/15889 | 2/2002 |
| WO | WO 02/47666 | 6/2002 |
| WO | WO 02/089777 | 11/2002 |

OTHER PUBLICATIONS

Korczyn, et al., Emerging Therapies in the Pharmacological Treatment of Parkinson's Disease, Drugs, 2002, 62(5) 775-786.*
Korczyn et al. Emerging Therapies in the Pharmcological Treatment of Parkinsons Disease, Drugs, 2002, 62(5) 775-786.*
Schneider, E.; "Kominierte Therapien;" *Neuro-Psychopharmaka*; vol. 5: Parkinsonmittel und Nootropika, pp. 131-133; ed. P. Riederer, et al., Springer Verlag, Vienna (1992).

(Continued)

*Primary Examiner* — Anand Desai
*Assistant Examiner* — Melissa Mercier
(74) *Attorney, Agent, or Firm* — D. Peter Hochberg; Sean F. Mellino

(57) ABSTRACT

The transdermal pharmaceutical preparations for the treatment of Parkinson's disease contain a combination of at least two active substances selected from the following groups of active substances: dopamine agonists and L-dopa, monoamine oxidase inhibitors, anticholinergics, NMDA-receptor antagonists, sympathomimetics; at least two of the said active substances being members of different active substance groups.

11 Claims, No Drawings

(56) References Cited

OTHER PUBLICATIONS

Sudo, et al.; Transdermal Absorption of L-dopa from Hydrogel in Rats; *Eur. J. Pharm. Sci.*; 7 (1998), pp. 67-71.

Reiderer, P., et al.; "Neuro-Psychopharmaka, Bd 5;" (1992), Springer Verlag, Wien.

Mucke, H.A.M.; "Rotigotine Schwarz Pharma;" Idrugs, Current Drugs Ltd., GB; vol. 6, No. 9 (2003), pp. 894-899.

Tuite, P., et al.,; "Recent Developments in the Pharmacological Treatment of Parkinson's Disease;" Expert Opinion on Investigational Drugs, Ashley Publications Ltd., London, GB, vol. 12, No. 8; Aug. 1, 2003; pp. 1335-1352.

Abramsky, O., et al.; "Combined Treatment of Parkinsonian Tremor with Propranolol and Levodopa;" *Journam of The Neurological Sciences*; Dec. 1971; vol. 14, No. 4; pp. 491-494.

Charles, P.D., et al.; "Classification of Tremor and Update on Treatment;" *American Family Physician*, American Academy of Family Physicians (U.S.); vol. 59, No. 6; Mar. 15, 1999; pp. 1565-1572.

Iravani, Mahmoud, M., et al.; "3,4-Methylenedioxymethamphetamine (Ecstasy) Inhibits Dyskinesia Expression and Normalized Motor Activity in 1-methyl-4phenyl-1,2,3,6 tetrahydropyridine-treated primates;" *Journal of Neuroscience*; vol. 23, No. 27; Oct. 8, 2003; pp. 9107-9115.

Rupniak; Therapeutic efficacy of a novel transdermal delivery system for (+)-PHNO in parkinsonian squirrel monkeys; J Neurol Neurosurg Psychiatry (1989) V. 52, No. 2, p. 289-90.

"Amitriptyline" in:National Library of Medicine, Specialized Information Services. Im Internet < http://chem2.sis.nlm.nih.gov/chemidplus/jsp/chemidlite/ChemFull.jsp >, 2004.

Potential of Transdermal Drug Delivery in Parkinson's Disease Drugs Aging, 2002, 19 (8), 561-570.

"Dopamine agonists and neuroprotection in Parkinson's disease;" European Journal of Neurology (2002); vol. 9, suppl. 3, pp. 7-14.

Naohide Inoue, et al.; A new idea of a drug therapy in Parkinson's disease—MAO-B inhibitor selegiline hydrochloride therapy; J. of Progress of Medicine; vol. 199, No. 4, pp. 289-292 (Oct. 27, 2001).

\* cited by examiner

TRANSDERMAL PHARMACEUTICAL PREPARATION CONTAINING ACTIVE SUBSTANCE COMBINATIONS, FOR TREATING PARKINSON'S DISEASE

CROSS-REFERENCE TO RELATED APPLICATIONS

This application is a National Stage application of International Application No. PCT/EP2004/009136, filed on Aug. 14, 2004, which claims priority of German application number 103 38 174.0, filed on Aug. 20, 2003.

BACKGROUND OF THE INVENTION

Field of the Invention

The invention relates to transdermally administrable pharmaceutical preparations for treating Parkinson's syndrome, said preparations containing a combination of at least two active substances which are suitable for use in the therapy of Parkinson's syndrome. The invention further relates to the use of such an active substance combination for the manufacture of a transdermally administrable medicament for treating Parkinson's disease, as well as to the therapeutic treatment of Parkinson patients by transdermally administering one of the said pharmaceutical preparations.

Active substances from the following groups are currently being utilised in the drug therapy of Parkinson's disease: anti-Parkinson agents having dopaminergic effect, especially L-dopa and dopamine receptor antagonists; centrally active anti-cholinergic agents (muscarine receptor antagonists); monoamine oxidase inhibitors; NMDA antagonists; beta-sympatholytics.

Apart from the above, administration of sympathomimetics from the group of the phenylethylamine derivatives (e.g. Ecstasy=MDMA) is being taken into consideration, as in some patients who are suffering from dyskinesias after long-term use of L-dopa, an improvement of the symptoms has been observed.

The most potent and most important Parkinson medicament is L-dopa (Levodopa), which is almost exclusively administered orally, preferably in combination with decarboxylase inhibitors (e.g. benserazide, carbidopa) or inhibitors of catechol-O-methyl transferase (e.g. entacapon). However, long-term use of L-dopa leads to the occurrence of dyskinesias, active substance fluctuations and loss of action. For this reason, one aims at keeping the dose of L-dopa as low as possible, or, at the beginning of the treatment, to dispense with the use of L-dopa entirely. For example, the time of beginning with an obligatory administration of L-dopa can be delayed by administering the monoamine oxidase inhibitor L-deprenyl (=selegiline). Likewise, an accompanying therapy with selegiline can make a reduction of the L-dopa dose by 25-30% possible. Furthermore, it has been observed that in younger Parkinson patients, in particular, it is possible to suppress the occurrence of dyskinesias, which are felt to be very bothersome, by early administration of selegiline.

Apart from L-dopa, dopamine-agonistically active substances such as, for example, lisuride, bromocriptine, pramipexol, ropinirole, rotigotine, terguride, cabergoline, apomorphine, piribedile, PHNO (4-propyl-9-hydroxynaphthoxazine) are used in the therapy of Parkinson's disease. The transmitter dopamine can to a large extent be substituted with such dopaminergically active substances.

An important role in the accompanying therapy of Parkinson's disease is played by the treatment with anticholinergically active substances (muscarine receptor antagonists), which particularly enables the suppression of the tremor. Substances of this group which are of therapeutical importance are, for example, bipreriden, trihexyphenidyl, procyclidine, bornaprine, metixene, orphenadrine, scopolamine, atropine and other belladonna alkaloids, benzatropine and nicotine.

Also suitable for the Parkinson therapy is a further group of active substances which are NMDA (N-methyl-D-aspartate) receptor antagonists; these include, for example, memantine and amantadine. These substances act synergistically with L-dopa and, in the case of a combination therapy, enable a reduction of the L-dopa dose. Akinesia in Parkinson patients, in particular, can be advantageously affected by additional administration of NMDA receptor antagonists.

The combination therapy of parkinsonism has been generally established, and the resultant advantageous effects are known (e.g. E. Schneider, "Kombinierte Therapien"; in: "Neuro-Psychopharmaka", vol. 5: Parkinsonmittel and Nootropika, pp. 131-144; ed. P. Riederer et al.; Springer Verlag, Vienna, 1992). In principle, the combination of oral medicaments is of disadvantage, however, since the effect obtained at a certain point in time is dependent on the, if anything, haphazard intrinsic kinetics of the active substance following oral absorption as a single dose. Since the individual active substances contained in an active substance combination differ in terms of their half-lives and oral dosage intervals, a uniform exposition of the patient to the different active substances does not result, rather there are wild fluctuations in the relative effects of each active substance component, depending on the changes occurring in the active substance levels over the course of the day.

Because of these known pharmacokinetic particularities, "fixed" active substance combinations within an oral administration form (e.g. tablets containing combined active substances) are regarded by the drug approval authorities as very problematic and are approved only in exceptional cases. Therefore, a combination therapy is generally carried through by separate administration of two or more mono-substance preparations. This, however, requires dosage intervals which are accurately adapted to the individual half-lives of these individual substances. It cannot be avoided in this case, however, that the respective active substance concentrations of the individual active substances, especially relative to one other, are subject to wild fluctuations. In addition, it is not always guaranteed that a patient or the nursing staff will strictly adhere to the dosage intervals. Non-compliance with the dosage scheme will possibly result in a considerable reduction of the advantageous effects of the combination therapy.

A further disadvantage of the oral combination therapy is that the simultaneous administration of different active substances increases the risk of undesirable side effects. These side effects often result from the temporary occurrence of plasma peak values shortly after oral administration.

Apart from oral Parkinson medicaments, transdermally administrable active substance preparations are also known, for example for L-dopa (Sudo et al.: Transdermal absorption of L-dopa from hydrogel in rats; Eur. J. Pharm. Sci. 7 (1998), 67-71), Rotigotin (EP-A-1 256 339), and deprenyl=selegiline (EP-B-0 404 807).

SUMMARY OF THE INVENTION

The object of the invention was to provide pharmaceutical preparations with which a combination therapy for Parkinson treatment can be carried out in a simple and secure manner, and which make it possible to avoid or alleviate the above-mentioned disadvantages. A further object of the invention was to indicate processes for the drug combination therapy of Parkinson's disease.

It has been found that the aforementioned objects are solved by transdermal pharmaceutical preparations containing a combination selected from the group consisting of a dopamine agonist and an anti-cholinergically active substance; L-dopa and an anticholinergically active substance; a dopamine agonist and an NMDA receptor antagonist; and L-dopa and an NMDA receptor antagonist. It has furthermore been surprisingly found that the addition to the foregoing combinations of at least one further substance selected from the group consisting of entacapone, benserazide and carbidopa is beneficial. It has also surprisingly been found that the addition to the foregoing combination of at least one active substance selected from the group consisting of beta blockers, the beta blockers being from the group consisting of propranolol, timolol, pindolol and atenolol is beneficial. Still an additional surprising finding was the improved treatment of Parkinson's disease having the foregoing combinations when the pharmaceutical preparation contains the active substances disclosed herein using the transdermal procedure.

DETAILED DESCRIPTION OF THE PRESENT INVENTION

According to the main claim, the inventive transdermal pharmaceutical preparations contain a combination of at least two active substances selected from the following groups of active substances:
  a) dopamine agonists and L-dopa,
  b) monoamine oxidase inhibitors,
  c) anticholinergics,
  d) NMDA-receptor antagonists,
  e) sympathomimetics.

At least two of the said active substances are members of different active substance groups. "Active substances" is understood to mean both the individual active substance compounds as such (e.g. free active substance bases) and their pharmaceutically acceptable salts and addition salts (e.g. acid addition salts). Furthermore the term "active substance", where applicable, refers both to the pharmacologically active, or more potent, enantiomer and to the corresponding racemic mixture.

In contrast to oral administration of an active substance combination, where the relative activities of the combination partners are, due to their different half-lives, subject to fluctuations, transdermal administration makes it possible to maintain a like-oriented increase and decrease in the plasma levels. Since with transdermal administration the occurrence of plasma peak values is largely avoided and the time course of the plasma concentrations is generally more constant, the risk of side effects occurring is reduced. Due to the more constant kinetics, especially where transdermal therapeutic systems are utilised for the controlled administration of active substance combinations, the advantageous effects of combined active substance administration are more reliably achieved than with oral administration. Particularly where transdermal therapeutic systems are used, compliance with the prescribed dosage schemes is facilitated and made safer.

It has surprisingly been found that combining active substances from two or more of the said active substance groups, which are based on different mechanisms of action, contributes to a superadditive combination of effects, and that these advantageous effects can be achieved by combined transdermal administration. In this way, active substance levels of the individual active substance components are obtained which are consistent and adapted to each other, thereby ensuring the safety of the combination therapy.

Moreover, it is possible, surprisingly, to use any adjustable combination of two active substances (according to the conditions mentioned in the main claim), so that, for certain groups of Parkinson patients, an adequate medicinal therapy can be made possible, depending, for example, on the stage of the disease or the type and severity of the symptoms.

The group of the dopamine agonists comprises, in particular, the active substances lisuride, bromocriptine, pramipexol, ropinirole, rotigotine, terguride, cabergoline, apomorphine, piribedile, pergolide, and 4-propyl-9-hydroxynaphthoxazine (PHNO).

The group of the monoamine oxidase inhibitors preferably consists of monoamine oxidase B (MAO-B)-selective inhibitors, with selegiline (=L-deprenyl) being particularly preferred. Selegiline is preferably used in the form of its acid addition salt, with the salts with halogen acids (e.g. selegiline hydrochloride) or with organic acids (e.g. selegiline citrate) coming into particular consideration. Selegiline is particularly suitable since it not only is a highly potent, selective and irreversible MAO-B inhibitor, but in addition inhibits the reabsorption of dopamine in catecholaminergic central neurons and has a certain protective action against the neurotoxic effects of 6-OH-dopamine. Transdermal administration is especially advantageous since, due to the first-pass metabolism being circumvented, it is possible to achieve markedly higher plasma levels—as compared to the corresponding oral doses—while the plasma concentrations of the metabolites (inter alia L-amphetamine, methamphetamine), which are rated as problematic, are clearly reduced.

From the group of the anticholinergics (muscarine receptor antagonists), the following active substances preferably come into consideration: bipreriden, trihexyphenidyl, procyclidine, bornaprine, metixene, orphenadrine, scopolamine, atropine and other belladonna alkaloids, benzatropine, and nicotine.

From the group of the NMDA receptor antagonists, memantine and amantadine preferably come into consideration.

The group of the sympathomimetics particularly contains active substances from the group of the phenylethylamine derivatives, with 3,4-methylenedioxymethamphetamine (=MDMA="Ecstacy") being particularly preferred.

According to a preferred embodiment, the pharmaceutical preparations according to the invention contain either
  a) at least one active substance from the group of the monoamine oxidase B inhibitors, preferably selegiline, in combination with at least one active substance from the group of the dopamine agonists, or
  b) at least one active substance from the group of the monoamine oxidase B inhibitors, preferably selegiline, in combination with L-dopa, or
  c) at least one active substance from the group of the monoamine oxidase B inhibitors, preferably selegiline, in combination with at least one active substance from the group of the dopamine agonists and in combination with L-dopa.

According to a further preferred embodiment, it is provided that an inventive transdermal pharmaceutical preparation contains a combination of two active substances, namely preferably
  a) a combination of a dopamine agonist and a monoamine oxidase B inhibitor, particularly selegiline, or
  b) a combination of L-dopa and a monoamine oxidase B inhibitor, particularly selegiline, or c) a combination of a dopamine agonist and an anticholinergically active substance, or
d) a combination of L-dopa and an anticholinergically active substance, or
e) a combination of a dopamine agonist and an NMDA receptor antagonist, or
f) a combination of L-dopa and an NMDA receptor antagonist.

According to a further preferred embodiment of the invention, the pharmaceutical preparations may contain a combination of three active substances, preferably
a) a combination of a dopamine agonist or L-dopa, an anticholinergically active substance, and an NMDA receptor antagonist, or
b) a combination of a dopamine agonist or L-dopa, an anticholinergically active substance and a monoamine oxidase B inhibitor, particularly selegiline.

In such a combination of three active substances, the dopamine agonist is responsible for the basic therapy of Parkinson's disease, whereas the anticholinergic substance can have a favourable influence on the tremor, and with the NMDA receptor antagonist an additional improvement of the akinesia can be achieved. The (additional) administration of selegiline, at the same time, has positive effects on the prevention of the progression of the disease, and the required dopamine agonist dose is, in addition, reduced.

According to a further preferred embodiment, an inventive pharmaceutical preparation contains a combination of selegiline with a dopamine agonist from the group comprising ropinirole, pramipexol and rotigotin. The combination of selegiline and rotigotin is particularly preferred.

It is furthermore advantageous if one of the above-described pharmaceutical preparations, especially a combination containing L-dopa, additionally contains at least one further active substance selected from the group comprising catechol-O-methyl transferase inhibitors and decarboxylase inhibitors, with entacapone, benserazide and carbidopa being particularly preferred.

Particularly for the treatment of Parkinson-induced tremor, it may be advantageous for a pharmaceutical preparation according to the invention to additionally contain at least one active substance from the group of the beta blockers, preferably from the group comprising propranolol, timolol, pindolol and atenolol.

The transdermal pharmaceutical preparations according to the invention may be produced in different formulations, known to the skilled artisan, which enable transdermal systemic active substance administration, for example as an ointment or gel. Preferably, the pharmaceutical preparations are formulated as transdermal therapeutic systems (TTS); the structure of such systems and the formulation adjuvants and other materials suitable for this purpose are known to the skilled artisan. Transdermal therapeutic systems enable the controlled release of active substances to the skin, at a predeterminable release rate and within a given period of time.

It has emerged that TTSs, due to their special properties, are particularly suitable for administration of active substance combinations in the treatment of Parkinson patients since the time course of the plasma levels of the individual active substance components is considerably more consistent than in oral administration and since, because of this, lower side effects are caused. In addition, by using active substance combination TTSs, the problem of compliance with the dosage intervals is considerably reduced, on the one hand because it is possible to administer two or more active substances together by applying a single TTS, on the other hand because a TTS can typically remain on the patient's skin over an application period of about 6 to 48 h. For example, treatment could be carried out by changing an active substance combination TTS once daily or every other day. This considerably facilitates application, compared to oral combination therapy with monosubstance preparations.

The TTSs according to the invention are preferably formulated as active substance plasters which adhere to the skin by briefly applied pressure; the active substance combination is, possibly together with further adjuvants, contained in an active substance reservoir which is either of the matrix type or has the shape of a bag. The structure of the TTSs additionally comprises an active substance-impermeable backing layer, as well as a likewise active substance-impermeable, peelable protective film.

The aforementioned bag-shaped reservoir is filled with a liquid, high-viscous, semi-solid or thixotropic matrix; more particularly it may be formulated as a gel. The back side of the bag, which is averted from the skin, must in this case be active substance-impermeable, and the side facing the skin must be active substance-permeable. Optionally, an active substance-permeable membrane (control membrane) may have the function of controlling the active substance release. Materials and adjuvants suitable for this purpose are known to those skilled in the art.

Particularly preferred are TTSs containing the active substance combination in a solid matrix. In the simplest case, a TTS according to the invention can be obtained by dispersing or dissolving, coarsely (i.e. particulately), colloidally or molecularly, one of the above-described active substance combinations in a solution of matrix base polymers and coating this mixture onto a suitable support—generally a siliconised thermoplastic film (later on serving as protective layer). After drying or evaporation of the solvent portions, the resultant layer, which represents the pressure sensitive-adhesive active substance reservoir, is covered with a further film, which later on represents the back layer of the TTS. Subsequently, TTSs of the desired geometric shape can be obtained from this laminate by punching out flat shapes.

Suitable as the back layer are, above all, polyesters, but also almost any other skin-friendly plastics, such as, for example, polyvinyl chloride, ethylene vinyl acetate, vinyl acetate, polyethylene, polypropylene, cellulose derivatives, and many others. In individual cases, the back layer may be provided with an additional layer, e.g. by vapour-deposition of metals or other diffusion-blocking additives, such as silicon dioxide, aluminium oxide or similar substances known to the skilled artisan.

The same materials can be used for the detachable protective film as for the back layer, provided that said film has been rendered detachable by a suitable surface treatment, e.g. siliconization.

Base polymers suitable for the manufacture of the matrix layer(s) are, above all, polymers based on acrylic acid and esters thereof, polyacrylates, isobutylene, ethylene vinyl acetate, rubbers, mixtures of rubbers and resins, cellulose derivatives, especially methyl celluloses and ethyl celluloses, styrene-diene copolymers, synthetic rubbers, pressure-sensitive silicone adhesives or hot-melt adhesives. Suitable mixtures of the stipulated polymers can also be employed to advantage. The term "hot-melt adhesive" includes any adhesives which are liquefied not by solvents but by melting at elevated temperatures, for example in the range from 60-200° C. Suitable as hot-melt adhesives are, for example, mixtures of esters of hydrogenated colophony with cellulose derivatives.

The TTSs according to the invention may optionally contain further adjuvants, especially from the groups of the skin permeation enhancers, the plasticizers, the tackifiers, the pH regulators, and the antioxidants.

Suitable as permeation-enhancing substances are, first of all, substances from the groups of the fatty alcohols, the fatty acids, the polyoxyethylene fatty alcohol ethers, the polyoxyethylene fatty acid esters, the fatty alcohol esters, and the fatty acid esters, particularly sorbitan monolaurate, or esters of long-chain fatty acids with methyl, ethyl or isopropyl alcohol, or esters of fatty alcohols with acetic acid or lactic acid. Substances such as oleic acid diethanolamine also come into consideration. The constituent amount of these substances is 0.1 to 25%-wt., preferably from 1 to 10%-wt., in each case relative to the overall weight of the active substance matrix.

The production of TTSs which contain a preferred active substance combination comprising the active substance selegiline can be carried out according to the processes described in the U.S. Pat. Nos. 5,462,746 and 5,902,601. Selegiline base is liquid and at room temperature readily volatile, which makes the manufacture of TTSs more difficult. The non-volatile hydrochloride of selegiline is less suitable due to its poorer skin permeability.

According to U.S. Pat. No. 5,462,746, selegiline hydrochloride is mixed with a solution of the matrix base polymers (e.g. pressure-sensitive adhesive polymers), and this mixture is coated on a support. The dried layer is covered with a second matrix layer containing basic groups that are capable of releasing the free base from the active substance salt.

According to U.S. Pat. No. 5,902,601 (or DE-A 43 32 094), the matrix base polymers are dissolved in the liquid, readily volatile active substance or adjuvant and coated on a support. On this layer are laminated one or more further matrix layers which contain no such readily volatile substance. Due to the migration of the active substance or adjuvant into the further matrix layer(s), an active substance matrix is obtained that is altogether shear-stable.

The invention thus also encompasses TTSs which are prepared by laminating at least two layers, each containing at least one active substance, wherein to produce a first layer a readily volatile active substance or adjuvant (e.g. selegiline base) is used as the solvent for the matrix base material, and wherein said layer is laminated to a second layer which has been produced without the use of a readily volatile active substance or adjuvant, and wherein due to the diffusive migration of the readily volatile active substance or adjuvant into the said second layer, a shear-stable composite and a matrix of unitary appearance is obtained.

The said at least two active substances of the active substance combination may be contained in the same matrix layer of the active substance reservoir. According to a preferred embodiment, it is provided for the individual active substances of this combination, but at least for two active substances of the combination, to be contained in different layers or compartments of the TTS.

The TTSs according to the invention preferably have a surface area in the range from 5 to 50 cm$^2$; the overall active substance content, relative to the active substance-containing reservoir, preferably amounts to 0.1 to 50%-wt., preferably 1 to 10%-wt. The active substance release rate preferably amounts to at least 0.1 mg/cm$^2$d; the daily dose released, relative to the active substance combination, is in the range from about 0.1 mg to 50 mg. The release rate and the daily dose can be adjusted so as to be different for the individual components, depending on the intended therapeutic effect.

The TTSs according to the invention enable the controlled, constant release of an active substance combination over a period preferably in the range from 0.5 to 7 days, especially 1 to 3 days.

The invention additionally encompasses the use of a combination of at least two anti-Parkinson active substances, as defined above, for the production of transdermally administrable medicaments, especially TTSs, which are suitable for the treatment of Parkinson's disease.

Furthermore, the invention also indicates processes for the therapeutic treatment of Parkinson patients; these processes are based on the administration of an active substance combination, as defined above, via the transdermal route to a person affected by the said disease.

This active substance combination is preferably administered in the form of TTSs which are changed in certain time intervals (e.g. twice daily, daily, every other day, etc.).

According to a further embodiment it is provided that the individual active substance components of the active substance combination are administered by means of two or more TTSs, which are applied individually to the skin of the patient being treated and each of which contains at least one active substance of the active substance combination.

The present invention makes the combination therapy of Parkinson's syndrome easier and safer and opens up additional and more diverse possibilities of application.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A transdermal pharmaceutical preparation for the treatment of Parkinson's disease containing a combination of two active substances, wherein said pharmaceutical preparation is a transdermal therapeutic system in the form of an active substance patch adhering to the skin, and the transdermal therapeutic patch contains said combination in a solid polymer matrix, and wherein said pharmaceutical preparation contains a combination of L-dopa and an anticholinergically active substance, said anticholinergically active substance being selected from the group consisting of bornaprine and metixene; and wherein said transdermal therapeutic system comprises different layers for containing said combination of two active substances, and wherein said two active substances of the active substance combination are contained in said different layers of the transdermal therapeutic system.

2. The pharmaceutical preparation according to claim 1, wherein said pharmaceutical preparation further contains an active substance selected from the group of the sympathomimetics.

3. The pharmaceutical preparation according to claim 2, wherein the group of sympathomimetics comprises an active substance selected from the group consisting of the phenylethylamine derivatives.

4. The pharmaceutical preparation according to claim 1, wherein said pharmaceutical preparation additionally contains at least one further active substance selected from the group consisting of catechol-O-methyl transferase inhibitors and decarboxylase inhibitors.

5. The pharmaceutical preparation according to claim 1, wherein said pharmaceutical preparation additionally contains at least one active substance selected from the group consisting of the beta blockers.

6. The pharmaceutical preparation according to claim 3, wherein said phenylethylamine derivatives are, 3,4-methylenedioxymethamphetamine.

7. The pharmaceutical preparation according to claim 4, wherein said at least one further active substance is selected from the group consisting of entacapone, benserazide and carbidopa.

8. The pharmaceutical preparation according to claim 5, wherein said beta blockers are selected from the group consisting of propranolol, timolol, pindolol and atenolol.

9. The pharmaceutical preparation according to claim 1, further containing an active substance selected from the group consisting of biperiden, trihexyphenidyl, procyclidine, scopolamine, atropine, benztropine and nicotine.

10. The pharmaceutical preparation according to claim 1, wherein a daily dose of said active substance combination released from said preparation is in the range of from 0.1 mg to 50 mg.

11. A transdermal pharmaceutical preparation for the treatment of Parkinson's disease containing a combination of two active substances, wherein said pharmaceutical preparation is a transdermal therapeutic system in the form of an active substance patch adhering to the skin, and the transdermal therapeutic patch contains said combination in a solid polymer matrix, and wherein said pharmaceutical preparation contains a combination of L-dopa and an anticholinergically active substance, said anticholinergically active substance being selected from the group consisting of bornaprine and metixene; and wherein said transdermal therapeutic system comprises at least two layers for containing said combination of two active substances, and wherein said two active substances of the active substance combination are contained in said at least two layers of the transdermal therapeutic system.

* * * * *